United States Patent
Anhalt

(10) Patent No.: US 11,766,166 B2
(45) Date of Patent: Sep. 26, 2023

(54) ENDOSCOPE EYEPIECE GRASPING MECHANISM AND ENDOSCOPE CAMERA HEAD WITH ENDOSCOPE EYEPIECE GRASPING MECHANISM

(71) Applicant: KARL STORZ SE & Co. KG, Tuttlingen (DE)

(72) Inventor: Thomas Anhalt, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 0 days.

(21) Appl. No.: 17/353,106

(22) Filed: Jun. 21, 2021

(65) Prior Publication Data

US 2022/0400935 A1 Dec. 22, 2022

(51) Int. Cl.
*A61B 1/00* (2006.01)
*A61B 1/04* (2006.01)

(52) U.S. Cl.
CPC ...... *A61B 1/00195* (2013.01); *A61B 1/00112* (2013.01); *A61B 1/042* (2013.01)

(58) Field of Classification Search
CPC . A61B 1/00112; A61B 1/00195; A61B 1/042; A61B 1/00105
See application file for complete search history.

(56) References Cited

U.S. PATENT DOCUMENTS

| 4,323,304 A * | 4/1982 | Ishii | G02B 7/02 396/17 |
| 2011/0317274 A1* | 12/2011 | Faber | A61B 1/00126 359/643 |
| 2019/0167374 A1* | 6/2019 | Calavrezos | A61B 1/0014 |

* cited by examiner

*Primary Examiner* — Aaron B Fairchild
(74) *Attorney, Agent, or Firm* — McGlew and Tuttle, P.C.

(57) ABSTRACT

An endoscope eyepiece grasping mechanism includes a base part engaging a tab member via a connected engagement member. An annular part has an outer engagement surface and an inner camming surface disposed coaxially with the base part and axially moveable relative to the base part. The engagement surface is moveable with the camming surface to move the tab member radially outwardly, with a movement of the annular part relative to the base part in a first axial direction, toward a receiving position, and to move the tab member radially inwardly, with movement of the annular part relative to the base part in a second axial direction, toward a grasping position. A biasing device acts to bias the annular part toward the grasping position. An endoscope eyepiece is engaged by the tab member upon the annular part moving from the receiving position to the grasping position.

12 Claims, 4 Drawing Sheets

ENDOSCOPE EYEPIECE GRASPING MECHANISM AND ENDOSCOPE CAMERA HEAD WITH ENDOSCOPE EYEPIECE GRASPING MECHANISM

TECHNICAL FIELD

The present invention relates generally to endoscopic camera devices and more particularly to a grasping mechanism or coupler to be fixed on a camera head device or similar optical device to couple the device with an optical endoscope.

TECHNICAL BACKGROUND

Endoscopic devices are used in the medical field for observing inside of a patient's body cavity. Such endoscopic devices include an insertion unit to be inserted into a patient's body cavity, a light source device that supplies light to the insertion unit that shines onto a target of observation and a removable camera head which is coupled to an eyepiece at the base of the endoscope. The camera head may be associated with a control device that controls the camera head as well as a display device that displays images produced by the camera head imaging device such as a CCD, CMOS or similar imaging device.

Camera heads are often provided with a grasping mechanism to grasp the eyepiece of an endoscope to effectively couple the endoscope to the camera head. Current grasping mechanism include a rotatable coupling feature. For clinicians/surgeons that rotate the scope within the grasping mechanism, this can cause the scope to inadvertently become decoupled from the camera head. Also, for camera heads with rotatable focus or zoom control, a rotatable grasping mechanism presents another rotatable feature adding to confusion or unwanted adjustment or decoupling. Additionally, some cameras (pendulum models) are designed specifically with the grasping mechanism allowed to freely rotate about the optical axis. Using a rotatable coupling feature then requires an additional rotational lock feature in order to insert or remove endoscopes. Further, twist on and off grasping mechanisms use more parts including many machined parts which entails higher costs.

SUMMARY OF THE INVENTION

It is an object of the invention to provide an endoscope eyepiece grasping mechanism (coupling feature) that comprises a push-pull mechanism so as to eliminate the problems of unwanted adjustment or decoupling associated with rotational mechanisms that provide grasping/coupling.

It is another object of the invention to provide a grasping mechanism (coupling feature) that avoids a need to rotationally lock the grasping mechanism, particularly on pendulum cameras, in order to insert or remove endoscopes from such a camera.

According to the invention, an endoscope eyepiece grasping mechanism is provided for an endoscope camera head. The endoscope eyepiece grasping mechanism comprises a base part with a central eyepiece receiving region with a light passage opening, the base part comprising an axially extending wall. A radially moveable tab member is positioned relative to the axially extending wall with an engagement member connected to the tab member. An annular part is provided comprising an outer engagement surface and an inner camming surface. The annular part is disposed coaxially with the base part and is axially moveable in an axial direction relative to the base part. The engagement surface is moveable with the camming surface to move the tab member radially outwardly, with a movement of the annular part relative to the base part in a first axial direction toward a receiving position, and to move the tab member radially inwardly, with movement of the annular part relative to the base part in a second axial direction toward a grasping position. In the grasping position an endoscope eyepiece within the central eyepiece receiving region is grasped by the grasping mechanism to couple the endoscope eyepiece to the endoscope camera head. A biasing device acts between the base part and the annular part to bias the annular part in the second direction toward the grasping position, whereby an endoscope eyepiece may be inserted in the central eyepiece receiving region in the receiving position and the endoscope eyepiece is engaged by the tab member and retained in the eyepiece receiving region upon the annular part moving from the receiving position to the grasping position.

The tab member may have a ramped shaped surface configured to be contacted by the endoscope eyepiece with the annular part in the grasping position to push the ramped shaped surface radially outwardly with axial movement of the endoscope eyepiece into the eyepiece receiving region, thereby causing movement of the tab member radially outwardly and movement of the annular part toward the receiving position.

The inner camming surface may be configured as an axially extending camming wall portion defining a slot. The engagement member may comprise a pin at each side of the tab member. The axially extending camming wall portion may have a circumferential extent with a radially outwardly extending portion defining each slot. Preferably more than one tab member with pins is provided, such tabs being distributed about the circumferential extent of the grasping mechanism. The axially extending wall of the base part may comprise a pin guide configuration adjacent to a tab opening. The axially extending wall may extend circumferentially around the light passage opening with a plurality of tab openings distributed uniformly relative to a circumferential extent of the axially extending wall.

The annular part may comprise an outer shell with the outer engagement surface and an inner housing with the inner camming surface. The inner housing may comprise an axially extending camming wall portion with an annular shape have widened regions with an extent that is at least partially radial. The inner camming surface may be formed by a slot in each adjacent region. The engagement member may comprise a pin at each side of the tab member, each pin being received in one slot. Each widened region may have a tab member passage. The outer shell may have a gripping contour to facilitate being actuated by a hand of a user.

The annular part may be formed of metal or plastic. The base part may be formed of metal or plastic.

According to a further aspect of the invention, an endoscope camera head is provided comprising a camera head chassis and an endoscope eyepiece grasping mechanism having some or all of the features as discussed above.

According to a further aspect of the invention, an endoscope system is provided comprising an endoscope with an endoscope eyepiece, a camera head chassis and an endoscope eyepiece grasping mechanism having some or all of the features as discussed above.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
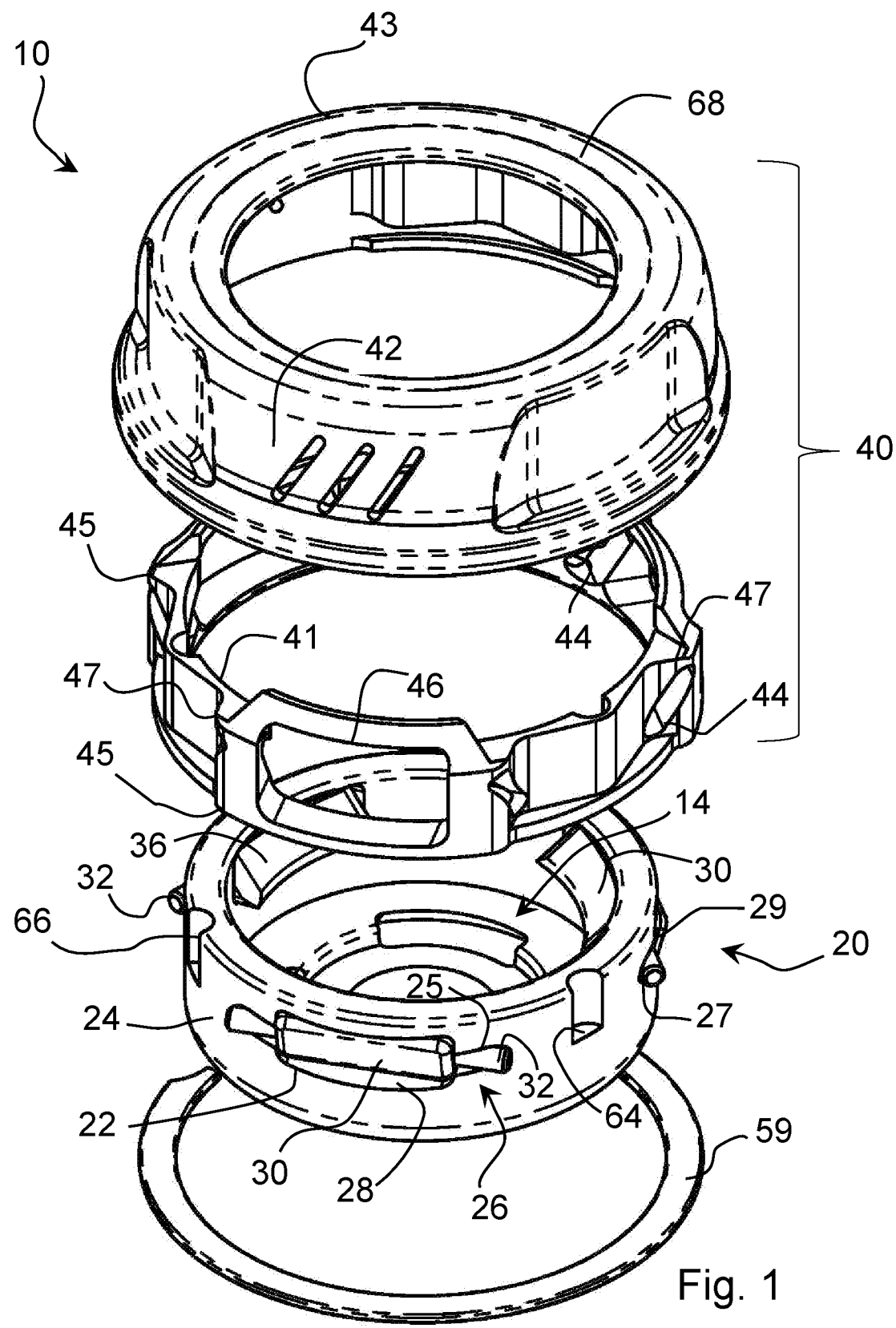
FIG. 1 is an exploded view showing an endoscope eyepiece grasping mechanism with features according to the invention.
Figure 3:
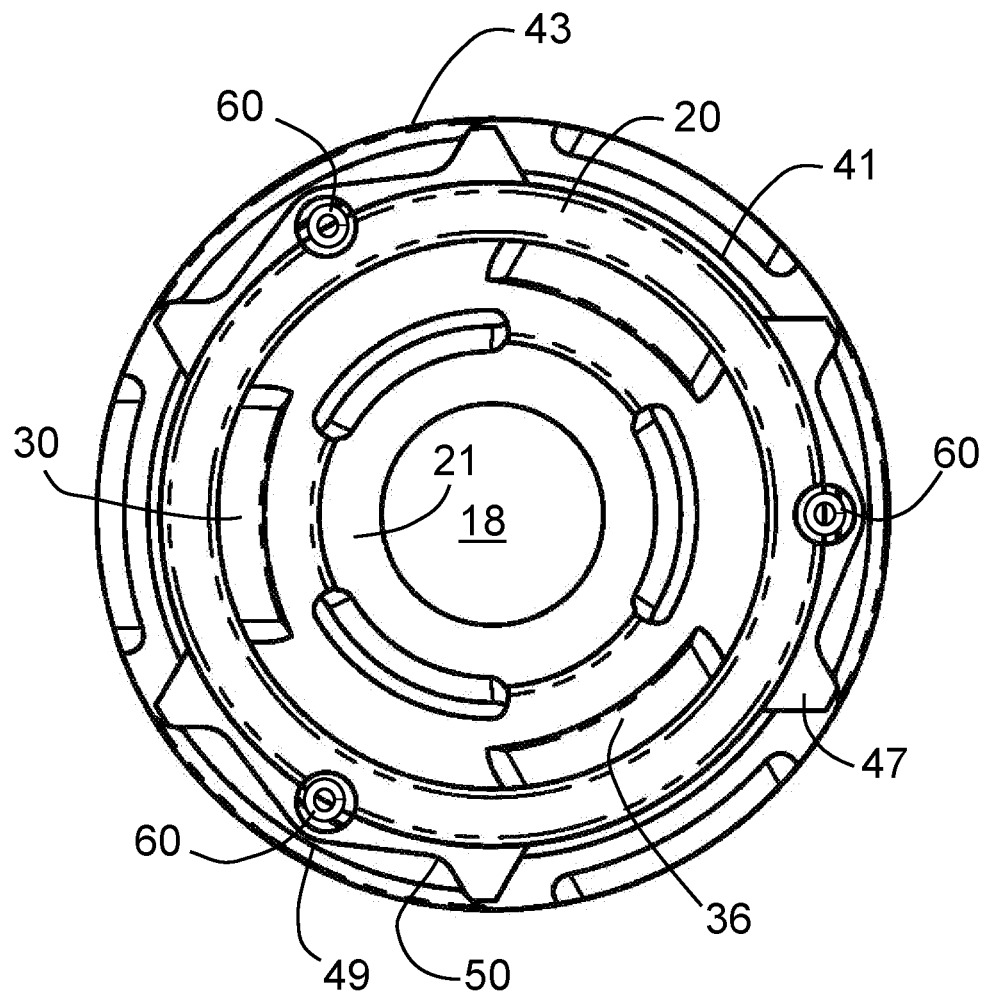
FIG. 3 is a top end view of the grasping mechanism shown without the outer shell.
Figure 4:
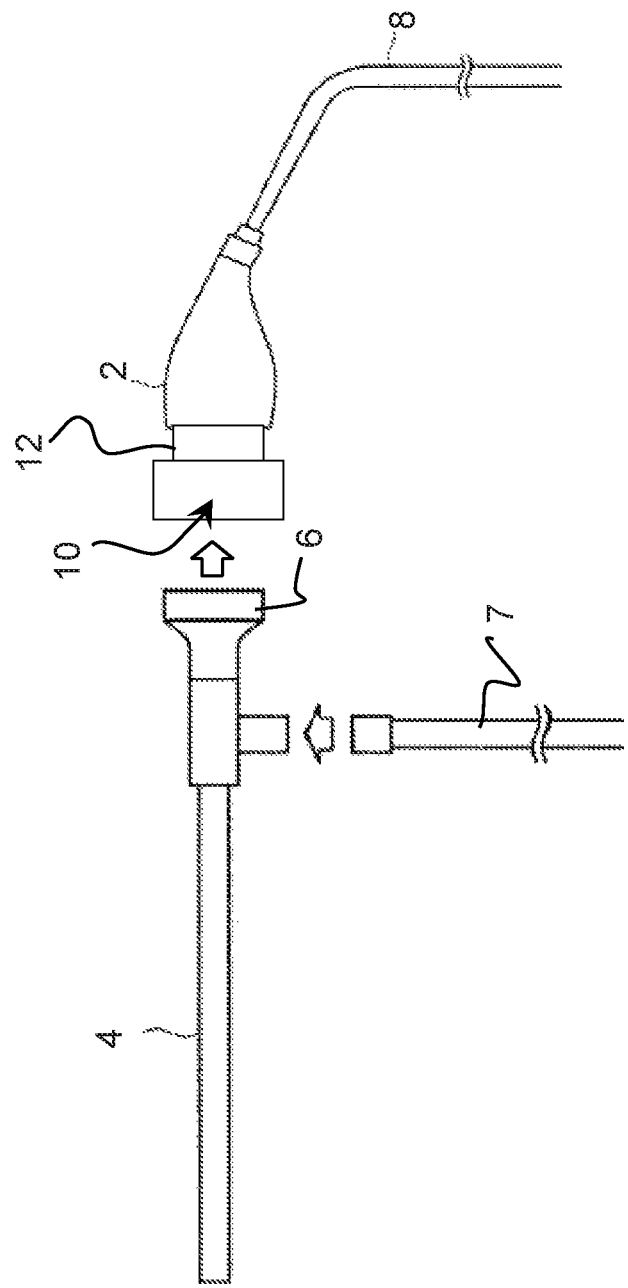
FIG. 4 is a schematic view illustrating a connection of a camera head having the endoscope eyepiece grasping mechanism of FIG. 1 with an endoscope having an endoscope eyepiece.

Referring to the drawings, FIG. 1 shows a grasping mechanism generally designated 10, which is attached to a mounting portion 12 of a camera head chassis 2 shown in FIG. 4. The grasping mechanism 10 comprises a base part 20 with a central eyepiece receiving region 14. The base part 20 defines a central light passage opening 18 (FIG. 3). The base part 20 comprises an axially extending wall 24 which extends fully around the light passage opening 18. The base part 20 also includes an inner contoured surface 21 that surrounds and defines the radially inward light passage opening 18. The contoured surface 21 is intended and configured to receive an endoscope eyepiece 6 in a coupled position, wherein the endoscope eyepiece 6 is grasped to retain the endoscope eyepiece 6 in the grasping mechanism 10 to couple an endoscope 4 to the camera head chassis 2.

The base part 20 supports at least one tab member 30. In the embodiment shown in FIGS. 1-4, three tab members 30 are positioned and guided by the base part 20. The axially extending wall 24 has a circumferential extent with tab guide regions 22 (three tab guide regions 22 are provided with the embodiment of FIGS. 1-5). The tab guide regions 22 have tab openings 28 with tab pin guide configurations 26, comprised of partially radially extending slot guides (angled slots) 25 at each side of each of the tab openings 28. The tab openings 28 and the extending slot guides 25 are formed in the wall 24. Each of the slot guides 25 define a path extending from a radially inward lower end 27 to a radially outward upper end 29. The path between the inward lower guide end 27 and the outward upper guide end 29 has a radial component relative to the inward light passage opening 18 based on the circumferential course of the wall 24.

Each tab member 30 includes a tab guide engagement member 32 in the form of two pins. One pin 32 extends from each side of each of the member tab 30. Each of the pins 32 is positioned in one of the slot guides 25 of one of the guide regions 22. The slot guides 25 are preferably provided with the same shape and define a region for movement of each pin 32. This moves the tab member 30 to follow the path of the movement of each pin 33 in the respective slot 25. The shapes of the slots 25 provide a radial path for a radial movement of each tab member 30 toward the light passage opening 18 and away from the light passage opening 18 to grasp and retain the endoscope eyepiece in the receiving region 14.

The grasping mechanism 10 further includes an annular part 40 with an outer engagement (grasping) surface 42 and a camming surface 44. In the embodiment of FIGS. 1-4, the outer engagement surface 42 is provided by an outer shell 43 with a gripping contour and the inner camming surface 44 is provided by an inner housing 41. The two parts (the inner housing 41 and the outer shell 43), are fixedly connected to form the annular part 40.

Figure 2:
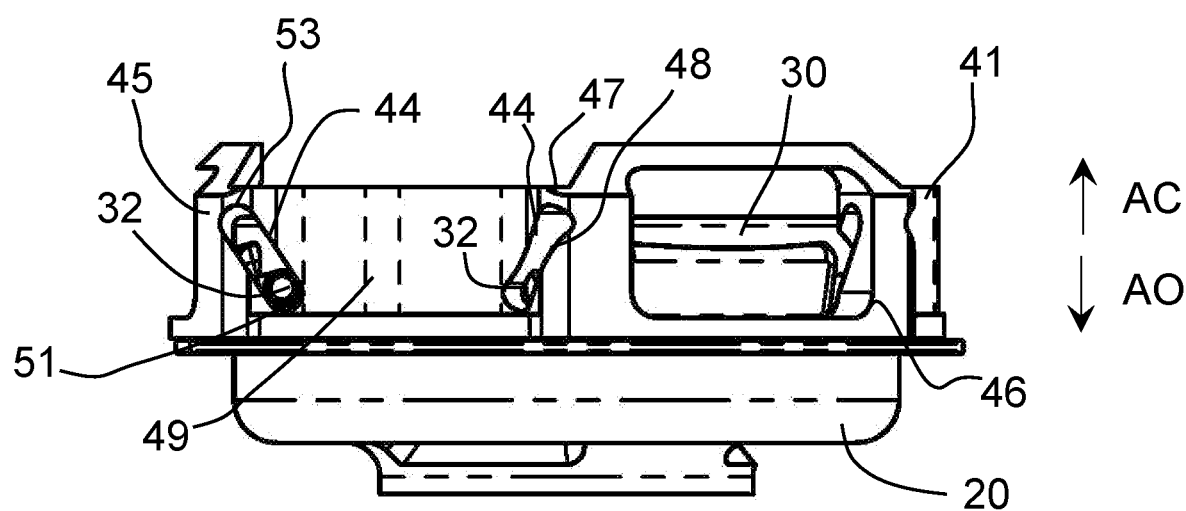
FIG. 2 is a side view of the grasping mechanism shown without an outer shell.

The inner housing 41 has an annular shape that includes widened regions 45 with tab passage openings 46 corresponding to the three tab guide regions 22 of the base part 20. In an assembled state of the grasping mechanism 10, the widened regions 45 are radially outward, relative to the centrally located passage opening 18, by a greater distance than reduced dimension (diameter) regions 50 of the inner housing 41. This provides partially radially extending adjacent regions 47, that each extend radially and circumferentially relative to the widened regions 45 of larger diameter and the reduced dimension region 50. At the radially extending regions 47 the inner camming surface 44 is provided in the form of slots 48 (FIG. 2). In the assembled state, each slot 48 receives one of the pins 32, with the slot 48 forming the camming surface 44 and the pins 32 being cam followers to follow the path defined by each slot 48. As shown, the slots 48 extend from a radially inward lower end 51 to a radially outward upper end 53. With this configuration, each pin 32 in the associated slot 48 is moved to a radially inward location of the associated slot guides 25 with the pin 32 at the radially inward lower end 51 of the respective slot 48. With the pin 32 at the radially outward end 53 of the respective slot 48, the pin 32 is moved to a radially outward location of the associated slot guide 25 of the tab guide configuration 26. In the assembled state, movement of the annular part 40 relative to the base part 20 in a first axial direction AO moves each of the tab members 30 radially outward (FIG. 2). Further, in the assembled state, movement of the annular part 40 relative to the base part 20 in a second axial direction AC moves each of the tab members 30 radially inward. In the assembled state, each tab member 30 is guided and positioned and supported for movement radially relative to the annular part 40, based on each tab member 30 being aligned with one of the tab passages 46.

A biasing device 60 is connected to each of the base part 20 and the annular part 42 to act between the base part 20 and the annular part 40. The biasing device 60 biases the annular part 40 in the axial direction AC toward a final grasping position with which the tab members 30 grasps the endoscope eyepiece 6 to hold the endoscope eyepiece in the central eyepiece receiving region 14 in contact with the inner contoured surface 21 so as to couple the eyepiece 4 with the camera head 2. In the grasping position, each pin 32 is at a radially innermost position and each pin 33 is at or toward the lower inner end 51 of each slot 48. In the embodiment shown, the biasing device comprises a plurality of helical compression springs 60. Each helical compression spring 60 is seated in a spring seat 64 and extends from the spring seat 64 between a spring receiving contour 66 of the annular part 40 and spring region 49 of the inner housing 41 to the an upper annular wall 68 of the outer shell 43. Each compression spring 60 acts between the respective spring seat 64 and a respective area of the upper annular wall 68.

For assembling the grasping device 10, the tab members 30 are each connected to pins 32 so one of the pins 32 extends from each side of each tab member 30. The pins 32 with connected tab members 30 are mounted on the base part 20 with the pins 32 received in one of the slot guides 25 of each pin guide configuration 26. The annular part 40 or the inner housing 41 is disposed coaxially with the base part 20 and pushed axially to capture the base part 20 within the inner housing 41, with each tab member 30 disposed in a corresponding one of the tab openings 46 of the inner housing 41. The assembly also captures each pin 32 in one of the slots 48 of the inner camming surface 44. The helical compression springs 60 are positioned on the respective spring seats 64 and then placed in contact with the inner surface of the upper annular wall 68 of the outer shell 43. A fixing of the outer shell 43 to the inner housing 41 may be performed before or after the inner housing 41 is combined with the base part 20. The entire assembly of the grasping device 10 is attached to the camera head chassis 2 via a threaded retaining feature of a known fastening mechanism with additional sealing provided by ring washer 59.

FIG. 4 shows the camera head 2 with the endoscope eyepiece grasping mechanism 10 along with a positioned endoscope 4. The endoscope 4 has the endoscope eyepiece 6. FIG. 4 also shows a light source 7 which can be connected to the endoscope 4 as well as a signal connection line 8 that is connected to the camera head 2.

As shown in FIG. 4, the endoscope eyepiece 6 of the endoscope 4 is moved axially toward the grasping mechanism 10 and then is moved into the eyepiece receiving region 14. In operation, the annular part 40 is grasped at the outer engagement surface 42 and is pulled in the direction AO. The angled slots 48 of the inner housing 41 act on the pins 32 such that the pins 32 each move radially outward along the slot guides 25 and move toward the radially outward end 53 of the angled slots 48. With this relative movement of the pins 32, each of the tab members 30 moves radially outward to a receiving position. After this, the annular part 40 may be released such that the action of the biasing device 60 moves the annular part 40 in the direction AC, such the grasping mechanism 10 assumes a grasping position. With this movement in the direction AC the angled slots 48 of the inner housing 41 act on the pins 32 such that the inner pins 32 each move radially inward along the slot guides 25 and move toward the radially inward end 51 of the angled slots 48. The pins 32 along with the tab members 30 move radially inward to the grasping position in which the tab members 30 engage an outer periphery of the endoscope eyepiece 6, to couple the endoscope eyepiece 6 to the camera head 2. To release the endoscope eyepiece 6 and the connected endoscope 4 from the camera head 2, the annular part 40 is again grasped and pulled in the direction AO to move the tab members 30 radially outwardly to a receiving position, allowing removal of the endoscope eyepiece 6 from the eyepiece receiving region 14.

The tab members 30 include ramped, shaped or contoured surface features 36 at an inward side, namely within the eyepiece receiving region 14 and facing and surrounding the light passage opening 18. This configuration allows the surface of the endoscope eyepiece 6 to be moved toward and into the receiving region 14 resulting in engagement with the tab members 30. Based on the surface of the eyepiece 6 acting on the contoured surface features 36 of the tab members 30, each of the tab members 30 is pressed radially outward to allow insertion of the endoscope eyepiece 6 into the receiving region 14. This movement and pressing of the tabs results in the annular part 40 being pulled down in the direction AO. This results in the annular part 40 sliding relative to the base part 20 from the grasping position to the receiving position. When the endoscope eyepiece is fully received in the receiving region 14, the surface of the eyepiece 6 clears the contoured surface features 36 of the tab members 30 and the tab members 30 again move radially inward with the annular part 40 sliding relative to the base part 20 from the receiving position to the grasping position to capture and retain the endoscope eyepiece 6 and to maintain the endoscope eyepiece 6 in the coupled position with the camera head 2.

While specific embodiments of the invention have been shown and described in detail to illustrate the application of the principles of the invention, it will be understood that the invention may be embodied otherwise without departing from such principles.

LIST OF REFERENCE CHARACTERS 2 camera head chassis
4 endoscope
6 endoscope eyepiece
7 light source
8 signal connection line
10 grasping mechanism
12 mounting portion
14 central eyepiece receiving region
18 light passage opening
20 base part
21 contoured surface
22 tab guide region
24 axially extending wall
25 slot guide
26 tab pin guide configuration
27 lower radially inner guide end
28 tab opening
29 upper radially outer guide end
30 tab member
32 engagement member (pin)
36 ramped/contoured surface features
40 annular part
41 inner housing/annular axially extending wall
42 outer engagement surface
43 outer shell
44 camming surface
45 widened region
46 tab member passage
47 adjacent region
48 slot
49 spring region
50 reduced dimension region
51 radially inward lower end
53 radially outward upper end
59 ring washer
60 biasing device—helical compression springs
64 spring seat
66 spring receiving contour
68 upper annular wall
AO first axial direction
AC second axial direction

What is claimed is:

1. An endoscope eyepiece grasping mechanism for attaching an endoscope camera head to an endoscope eyepiece, the grasping mechanism comprising:
a base part having a receiving region with an aperture configured to allow light passage, the base part being configured to be mountable on the camera head;
a tab member movably arranged within the base part;
an engagement member connected to the tab member;
an annular part having an outer surface and an inner surface, the inner surface being a camming surface, the annular part being arranged coaxial with the base part and bidirectionally movable along a coaxial axis relative to the base part such that the grasping mechanism has receiving and grasping states;

a biasing device arranged between the base part and annular part configured to bias the annular part towards an axial position relative to the base part where the grasping mechanism is in the grasping state, in the receiving state, the grasping mechanism is configured such that when the endoscope eyepiece is inserted in the receiving region, the tab member engages the endoscope eyepiece, in the grasping state, the grasping mechanism is configured such that the endoscope eyepiece, inserted when the grasping mechanism was in the receiving state, is then grasped by the tab member, connecting the endoscope eyepiece to the endoscope camera head, the grasping mechanism is configured such that:

moving the annular part relative to the base part such that the grasping mechanism is moved toward the receiving state, the tab member moves radially outward with respect to the coaxial axis, and moving the annular part such that the grasping mechanism moves toward the grasping state, the tab member moves radially inward with respect to the coaxial axis.

2. The endoscope eyepiece grasping mechanism according to claim 1, wherein the tab member has a ramped shaped surface configured to be contacted by a portion of the endoscope eyepiece when the annular part is arranged in the grasping state to push the ramped shaped surface radially outwardly with axial movement of the portion of the endoscope eyepiece into the receiving region, causing movement of the tab member radially outwardly and movement of the annular part toward the receiving state.

3. The endoscope eyepiece grasping mechanism according to claim 1, wherein the inner camming surface is formed by an axially extending camming wall portion defining a slot.

4. The endoscope eyepiece grasping mechanism according to claim 3, wherein:

the engagement member comprises a pin at each side of the tab member; and the axially extending camming wall portion has a circumferential extent with a radially outwardly extending portion defining the slot.

5. The endoscope eyepiece grasping mechanism according to claim 4, further comprising at least another tab member with pins to provide a plurality of tab members, wherein an axially extending wall of the base part comprises a pin guide configuration adjacent to a tab opening.

6. The endoscope eyepiece grasping mechanism according to claim 4, further comprising:

an axially extending wall extending circumferentially around the aperture;

a plurality of tab openings are arranged at positions distributed uniformly relative to a circumferential extent of the axially extending wall.

7. The endoscope eyepiece grasping mechanism according to claim 1, wherein the annular part comprises:

an outer shell with an outer engagement surface; and an inner housing with the camming surface.

8. The endoscope eyepiece grasping mechanism according to claim 7, wherein:

the inner housing comprises an axially extending camming wall portion with an annular shape having widened regions with an extent that is at least partially radial;

the camming surface is a surface defining a plurality of slots;

the engagement member comprises a pin at each side of the tab member, each pin being received in one of said plurality of slots; and each widened region has a tab member passage.

9. The endoscope eyepiece grasping mechanism according to claim 7, wherein the outer shell has a gripping contour configured to facilitate being actuated.

10. The endoscope eyepiece grasping mechanism according to claim 1, wherein:

the annular part is formed of metal or plastic; and the base part is formed of metal or plastic.

11. An endoscope camera head comprising:

a camera head chassis; and the endoscope eyepiece grasping mechanism according to claim 1.

12. An endoscope system comprising:

an endoscope with the endoscope eyepiece;

a camera head chassis; and the endoscope eyepiece grasping mechanism according to claim 1.

* * * * *